(12) United States Patent
Haibach et al.

(10) Patent No.: US 11,590,309 B2
(45) Date of Patent: Feb. 28, 2023

(54) INTERFACE DEVICE FORMABLE BY ADDITIVE MANUFACTURING PROCESS

(71) Applicant: KONINKLIJKE PHILIPS N.V., Eindhoven (NL)

(72) Inventors: Richard Thomas Haibach, Verona, PA (US); Peter Chi Fai Ho, Pittsburgh, PA (US); Lauren Patricia Chodkowski, Pittsburgh, PA (US); Jonathan Sayer Grashow, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 920 days.

(21) Appl. No.: 16/339,183

(22) PCT Filed: Oct. 4, 2017

(86) PCT No.: PCT/EP2017/075270
§ 371 (c)(1),
(2) Date: Apr. 3, 2019

(87) PCT Pub. No.: WO2018/065500
PCT Pub. Date: Apr. 12, 2018

(65) Prior Publication Data
US 2019/0307980 A1 Oct. 10, 2019

Related U.S. Application Data

(60) Provisional application No. 62/403,935, filed on Oct. 4, 2016.

(51) Int. Cl.
*A61M 16/06* (2006.01)
*B33Y 80/00* (2015.01)

(52) U.S. Cl.
CPC .... *A61M 16/0622* (2014.02); *A61M 16/0605* (2014.02); *B33Y 80/00* (2014.12); *A61M 2207/00* (2013.01)

(58) Field of Classification Search
CPC .......... A61M 16/0622; A61M 16/0605; A61M 16/00; A61M 16/06; A61M 16/0616;
(Continued)

(56) References Cited

U.S. PATENT DOCUMENTS 8,371,293 B2 * 2/2013 Henry ............... A61M 16/0605
623/7
9,044,564 B2 * 6/2015 Dravitzki .......... A61M 16/0616
(Continued)

FOREIGN PATENT DOCUMENTS

WO WO2016097948 A1 6/2016
WO WO2017142568 A1 8/2017

*Primary Examiner* — Justine R Yu
*Assistant Examiner* — Kelsey E Baller
(74) *Attorney, Agent, or Firm* — Michael W. Haas

(57) ABSTRACT

An interface device is structured to be connected in fluid communication with a source of breathing gas and to provide a flow of breathing gas to the airways of a patient. The interface device includes a support (24), a deformable portion (28) situated on the support, and an interface portion (32) situated on the deformable portion and being structured to be engaged with the patient in the vicinity of the airways, with the deformable portion including a plurality of deformable elements (36) that form a lattice structure and that are connected with the support at a plurality of spaced apart points of connection (44) on the support. The interface device may be formed via an additive manufacturing process.

11 Claims, 12 Drawing Sheets

(58) Field of Classification Search
CPC .......... A61M 16/0611; A61M 16/0633–0655; A61M 2207/00; A61M 2016/0661; B33Y 80/00; A62B 18/00; A62B 18/006–025; A62B 18/06–08

See application file for complete search history.

(56) References Cited

U.S. PATENT DOCUMENTS

| | | | |
|---|---|---|---|
| 9,072,855 B2* | 7/2015 | McAuley | A61M 16/0622 |
| 9,999,739 B2* | 6/2018 | Hendriks | A61M 16/0622 |
| 2007/0215161 A1* | 9/2007 | Frater | A61M 16/0622 |
| | | | 128/206.24 |
| 2010/0294281 A1* | 11/2010 | Ho | A61M 16/0633 |
| | | | 128/206.24 |
| 2012/0132208 A1 | 5/2012 | Judson | |
| 2013/0146060 A1 | 6/2013 | Ho | |
| 2013/0171019 A1 | 7/2013 | Gessler | |
| 2014/0163445 A1* | 6/2014 | Pallari | A61F 13/00029 |
| | | | 604/290 |
| 2015/0273170 A1* | 10/2015 | Bachelder | A61M 16/0611 |
| | | | 264/129 |
| 2015/0359986 A1 | 12/2015 | Skipper | |
| 2016/0184538 A1* | 6/2016 | Grashow | A61M 16/0051 |
| | | | 128/202.22 |
| 2019/0240436 A1 | 8/2019 | Romagnoli | |

\* cited by examiner

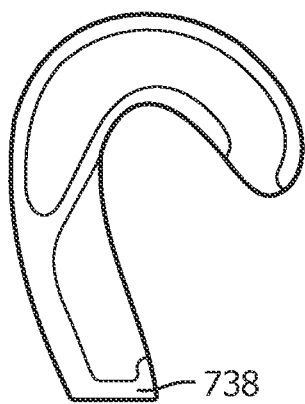
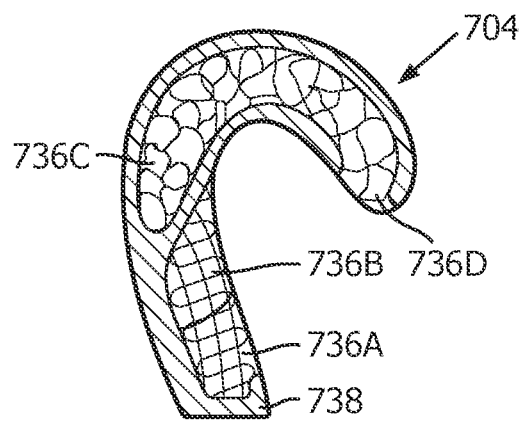
FIG. 10A  FIG. 10B
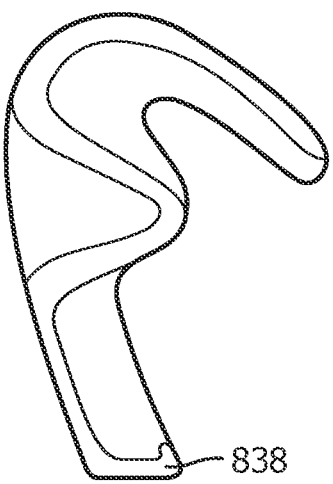
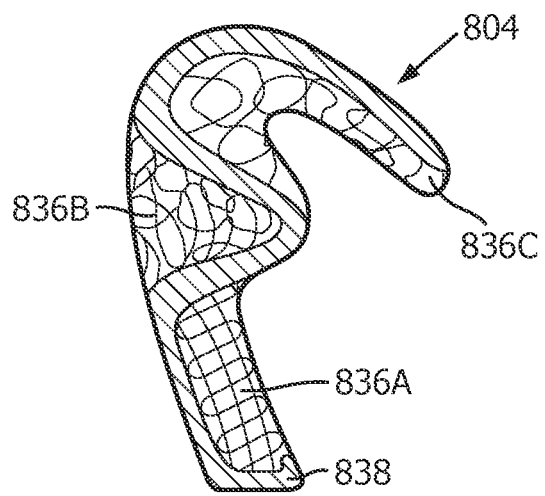
FIG. 11A  FIG. 11B

INTERFACE DEVICE FORMABLE BY ADDITIVE MANUFACTURING PROCESS

CROSS-REFERENCE TO RELATED APPLICATIONS

This patent application claims the priority benefit under 35 U.S.C. § 371 of international patent application no. PCT/IB2017/075270, filed Oct. 4, 2017, which claims the priority benefit under 35 U.S.C. § 119(e) of U.S. Provisional Application No. 62/403,935 filed on Oct. 4, 2016, the contents of which are herein incorporated by reference.

BACKGROUND OF THE INVENTION

1. Field of the Invention

The present invention relates to patient interface devices for transporting a gas to and/or from an airway of a patient and, in particular, to an interface device that is formable by an additive manufacturing process and that can be customized for a particular patient.

2. Description of the Related Art

Numerous situations exist where it is necessary or desirable to deliver a flow of breathing gas non-invasively to an airway of a patient, i.e., without intubating the patient or surgically inserting a tracheal tube in the esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder such as sleep apnea syndrome, in particular, obstructive sleep apnea (OSA), or congestive heart failure.

Non-invasive ventilation and pressure support therapies involve the placement of an interface device such as a patient interface device including a mask component on the face of a patient. The mask component may be, without limitation, a nasal mask that covers the patient's nose, a nasal cushion that rests beneath the patient's nose (such as a "pillows" style nasal cushion having nasal prongs that are received within the patient's nostrils or a "cradle" style nasal cushion that rests beneath and covers the patient's nostrils), a nasal/oral mask that covers the nose and mouth, or a full face mask that covers the patient's face. The patient interface device interfaces the ventilator or pressure support device with the airway of the patient so that a flow of breathing gas can be delivered from the pressure/flow generating device to the airway of the patient. It is known to maintain such devices on the face of a wearer by a headgear having one or more straps adapted to fit over/around the patient's head.

Due to the variability of shapes and sizes of the heads and faces of patients, numerous types and configurations of interface devices such as patient interface devices are available for selection by a professional to suit the needs of any given patient. However, any such device typically is intended to be worn by a large number of people having different head shapes and sizes, and thus any given device typically is not necessarily customized for any particular patient and rather is intended to fit a variety of patents. While some success has been achieved in selecting pre-designed interface devices for patients and achieving a reasonable fit with such patients, the fit is still, on the whole, at best only what can be reasonable achieved with a device that is intended for use with a range of head and facial sizes and shapes, which is not an optimum fit.

Furthermore, limitations with materials and manufacturing processes have resulted in interface devices and headgear that have had limitations with regard to fit and compliance in places where it is most desired. For example, the human face can have a complex shape, and a conventional strap or a homogeneous foam cushion often does not have the compliance that would be required in order to provide an optimum fit. Improvements thus would be desirable.

SUMMARY OF THE INVENTION

Accordingly, it is an object of the present invention to provide an interface device structured to be connected in fluid communication with a source of breathing gas and to provide a flow of breathing gas to the airways of a patient. The interface device can be generally stated as including a support, a deformable portion situated on the support, an interface portion situated on the deformable portion and being structured to be engaged with the patient in the vicinity of the airways, and the deformable portion including a plurality of deformable elements that form a lattice structure and that are connected with the support at a plurality of spaced apart points of connection on the support. The interface device may be formed via an additive manufacturing process.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 10A and 10B are schematic depictions of an interface device in accordance with an eighth embodiment of the present invention;

FIGS. 11A and 11B are schematic depictions of an interface device in accordance with a ninth embodiment of the present invention;

DETAILED DESCRIPTION OF EXEMPLARY EMBODIMENTS

Figure 1:
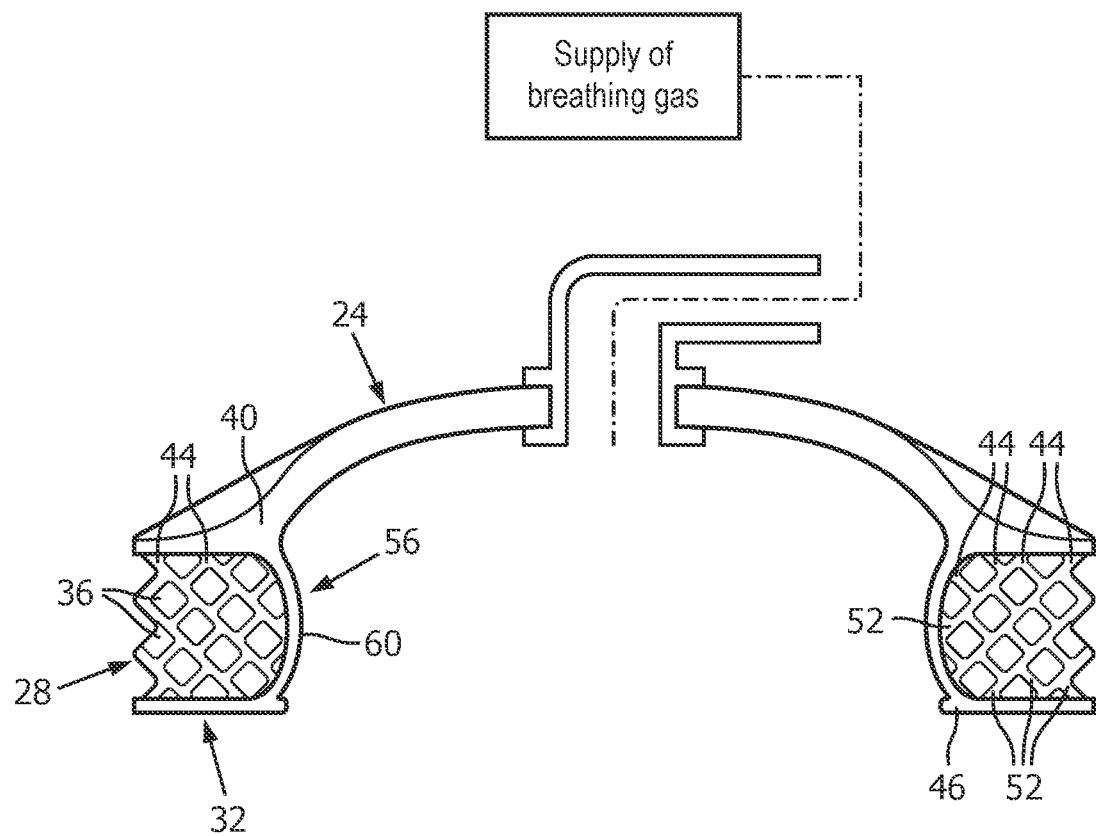
FIG. 1 is a side view, partially in section, of an interface device in accordance with a first embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1A:
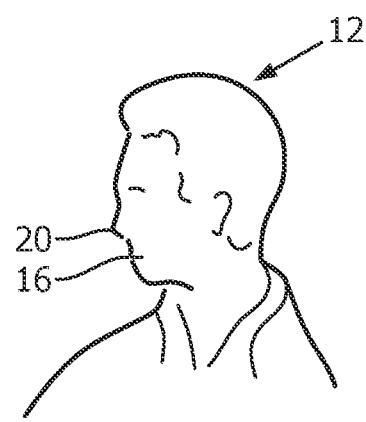
FIG. 1A is an exemplary side view of an exemplary patient.

An interface device 4 in accordance with a first embodiment of the present invention is depicted generally in FIG. 1. Interface device 4 is structured to be in fluid communication with a source of breathing gas 8 and is configured to interface a flow of breathing gas to the airways of a patient 12 such as is depicted generally in FIG. 1A. Patient 12 is an individual who is in need of respiratory therapy, and the airways of patient 12 are represented by a mouth 16 and the nostrils of a nose 20. As is understood in the relevant art, the flow of breathing gas that is supplied to the airways of patient 12 is at a positive pressure, i.e., a pressure in excess of atmospheric pressure.

interface device 4 can be said to include a support 24 which, in the depicted exemplary embodiment, includes an elbow that is pivotably mounted thereon for connection with source of breathing gas 8. Interface device 4 further includes a deformable portion 28 that is situated on support 24 and an interface portion 32 that is situated on deformable portion 28. Deformable portion comprises a plurality of deformable elements 36 that mutually interconnected and that together form a lattice structure that is configured to have predetermined deformation characteristics. The lattice structure can also be referred to as a plurality of pillars or one or more springy structures or deformable structures.

It can be seen that support 24 includes a base 40, and the plurality of deformable elements 36 are arranged such that they are connected with base 40 at a plurality of points of connection 44 with base 40 that are spaced apart from one another and by which the plurality of deformable elements 36 are connected with base 40. Such spacing apart of points of connection 44 with base 40 is a result of the lattice structure of mutually interconnected deformable elements 36.

It can be seen that interface portion 32 includes a wall 48 that is configured to engage the face of patient 12 in the vicinity of the airways. The plurality of deformable elements 36 further are connected with wall 48 at a plurality of additional points of connection with wall 48 that are likewise spaced apart from one another and by which the plurality of deformable elements 36 are connected with wall 48.

Interface portion 32 further includes a barrier apparatus 56 having a barrier 60 that extends between wall 48 and base 40. It can be seen that barrier 60 and the plurality of deformable elements 36 are disconnected from one another. It is noted, however, that barrier 60 and the plurality of deformable elements 36 could be connected together in other embodiments, and at least one such other embodiment is set forth below.

In accordance with an aspect of the present invention, at least deformable portion 28 is formed from an additive manufacturing process, of which many are known in the relevant art. For instance, polymer materials may be employed using an SLS (Selective Laser Sintering) process whereby successive layers of material are built, one upon the next, in order to form deformable portion 28 as a unitary and integrally formed single piece component. Furthermore, it is expressly noted that interface device 4 may itself be co-formed as a single piece integral member by co-forming support 24, deformable portion 28, and interface portion 32 together as a single piece unitary structure using the aforementioned additive manufacturing process. That is, while interface device 4 can itself be entirely manufactured as a unitary structure using the aforementioned additive manufacturing process, it is understood that, in other embodiments, less than the entirety of interface device 4 can be formed by the additive manufacturing process depending upon the needs of the particular application.

Interface device 4 and, more particularly, deformable portion 28, can be formed, by way of example, from one or more deformable polymers such as any one or more of PVC (vinyl), TPU (thermoplastic polyurethane), TPE (thermoplastic elastomer), TEBA (polyether block amide) or other appropriate material having desirable deformation characteristics, whether a metallic material or a non-metallic material. It is expressly noted that deformable portion 28 can be formed from a plurality of these materials or other materials. The plurality of materials may have different material properties such as a modulus of elasticity, yield strength, etc., without limitation, and the resultant deformable portion 28 can be a matrix in the form of a composite or an alloy, for instance, having material properties that are a hybrid of the materials from which it is formed.

Moreover, deformable elements 36 are configured in such a fashion, from the perspective of length, cross-sectional dimensions, density (i.e., spacing with respect to one another), and material properties such as modulus of elasticity, and the like, and in other ways to have desirable deformation characteristics and other characteristics at various locations along interface device 4. For instance, it may be desirable for interface device 4 to have greater compliance in the vicinity of the chin of patient 12, and deformable portion 28 may be configured such that the deformable elements 36 in the vicinity of the chin will be, for instance, thinner in cross section and/or spaced apart to a greater extent than elsewhere (thereby having a lesser density than elsewhere), or can be otherwise configured to provide greater compliance in the desired area. Reduced compliance (i.e., increased resistance to deformation) can be provided by increasing the stiffness of the various deformable elements 36, such as by making them of a greater cross-section and/or to be relatively shorter and/or to be of a greater positional density than elsewhere in deformable portion 28, by way of example.

In the depicted exemplary embodiment, barrier 60 and deformable elements 36 are disconnected from one another, whereupon base 40 will deform separately from the deformable elements 36 of deformable portion 28. That is to say, while barrier 60 and deformable elements 36 may deform simultaneously when interface device is received on the face of patient 12, the deformation of barrier 60 does not result in the deformation of deformable elements 36 and vice-versa. Barrier 60, being situated on the high pressure side of interface device 4, will advantageously resist the pressurized flow of breathing gas from flowing into the interstices between deformable elements 36, thereby advantageously keeping deformable portion 28 relatively cleaner than would likely otherwise be the case if the flow of breathing gas and the exhalation thereof were constantly flowing through the interstices of deformable portion 28.

The lattice structure formed by the plurality of deformable elements 36 not only enables the deformation characteristics of deformable portion 28 to have customizable compliance in desirable areas, such as the aforementioned chin area, the lattice structure formed by deformable elements 36 additionally can be customized to individual patients. For instance, patient 12 potentially could visit a professional for a customized evaluation of the profile of the face of patient 12, and interface device 4 could be custom configured such that deformable portion 28 provides customized fit and customized deformation characteristics that provide an optimized fit with patient 12. In this regard, it is understood that wall 48 engages the face of patient 12 in the vicinity of the airways, and wall 48 and deformable portion 28 can both be customized to suit the face of patient 12 depending upon the needs of the particular application. In this regard, any of a variety of criteria can be employed to determine whether customization of deformable portion 28 is desirable for patient 12.

It can also be seen that the mutually interconnected lattice structure formed by the plurality of deformable elements 36 would likely be very difficult to manufacture if it were not being manufactured by an additive manufacturing process. For instance, conventional injection molding processes and other material formation methodologies could not be employed to form certain structures due to undercuts in the structures and due to other configuration properties of such structures. However, the formation of such structures is made possible by using additive manufacturing.

The availability of such an additive manufacturing process to form interface device 4 thus advantageously enables deformable elements 36 and the lattice structure thereof to be customized as needed, whether to suit an individual patient or whether to provide customized compliance as a general matter that is suited to a plurality of patients. Moreover, the advantageous use of an additive manufacturing process enables deformable elements 36 to be manufactured as discrete deformable structures that would not be practical or perhaps even possible to form with other types of manufacturing methodologies. It thus can be understood that interface device 4, formed by the aforementioned additive manufacturing process or any other such additive manufacturing process, advantageously provides improved fit and function in a fashion that was previously unobtainable. Other advantages will be apparent.

Figure 2:
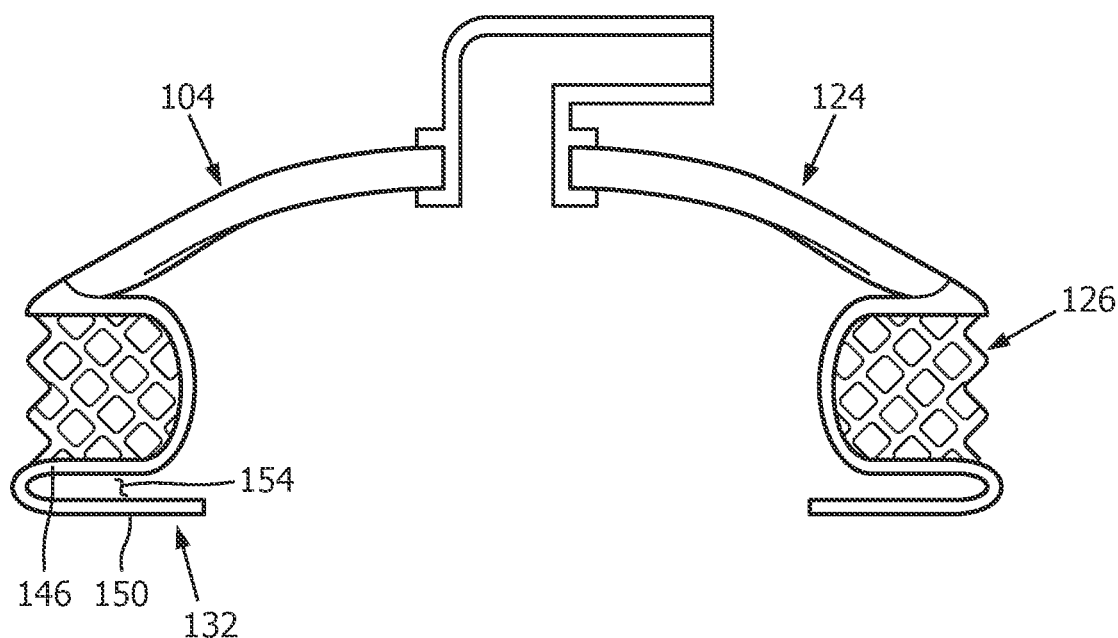
FIG. 2 is a side view, partially in section, of an interface device in accordance with a second embodiment of the present invention.

An interface device 104 in accordance with a second embodiment of the present invention is depicted generally in FIG. 2. Interface device 104 is similar to interface device 4 in that it includes a support 124, a deformable portion 128, and an interface portion 132 that are similar to that of interface device 4. However, interface portion 132 additionally includes a flap 150 that extends from a wall 148 of interface portion 132. While flap 150 is provided as a part of interface device 104, it is noted that flap 150 can be optional in other embodiments.

Flap 150 and wall 148 together advantageously provide enhanced engagement with and sealing with the face of patient 12. Specifically, interface portion 132 can be said to include a pocket 154 that is formed between flap 150 and wall 148. It can be understood that pocket 154 is in fluid communication with the high pressure region of interface device 104 and thus receives in pocket 154 the fluid pressure that exists inside interface device 104 when the flow of breathing gas is provided to the airways of patient 12. Such positive pressure inside pocket 154 tends to compress flap 150 away from wall 148 and against the face of patient 12 with increased engagement force that is in excess of what could be achieved from deformable portion 128 alone, at least in certain areas. For instance, sometimes in the region of the chin of patient 12 at the area of transition between the chin and the mandible, a conventional mask or other such device can have limited contact with patient 12 in such a difficult area depending upon the geometry of the face of patient 12. However, by providing flap 150 and thus likewise providing pocket 154, flap 150 can be engaged with the face of patient 12 due to the inflation of pocket 154 by the positive pressure of the flow of breathing gas impinging on the flap 150 within pocket 154. Flap 150 thereby advantageously provides a fluid seal between interface device 104 and the face of patient 12. Other advantages will be apparent.

Figure 3:
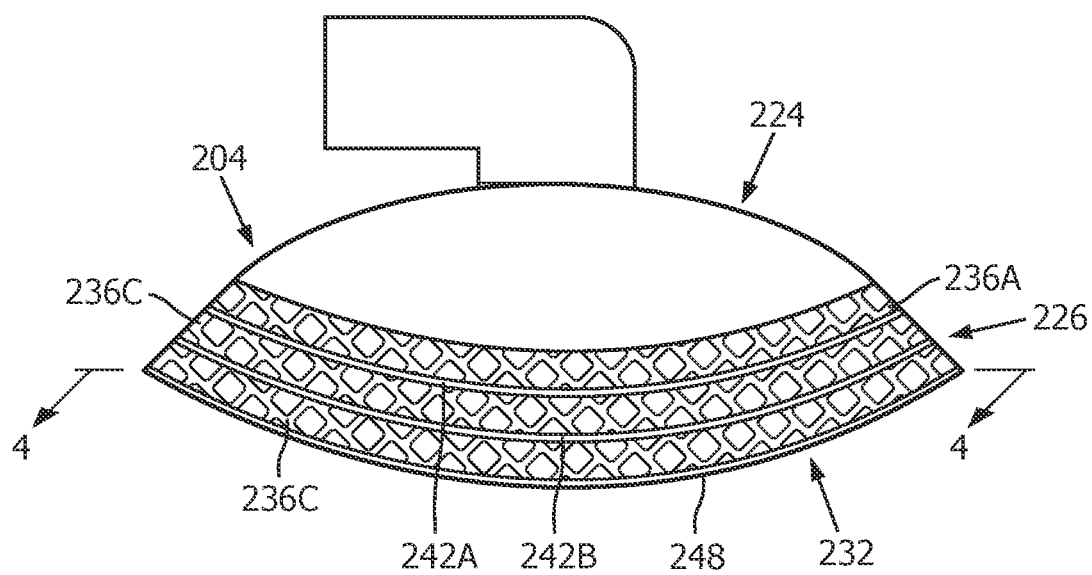
FIG. 3 is a side view of an interface device in accordance with a third embodiment of the present invention.
Figure 4:
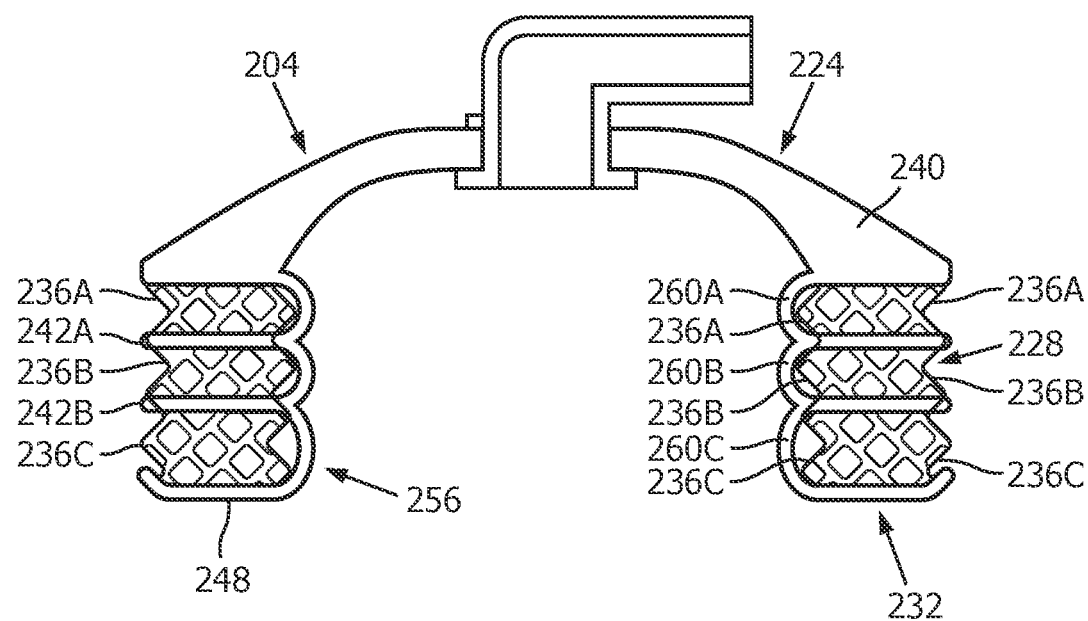
FIG. 4 is a sectional view as taken along line 4-4 of FIG. 3.

An interface device 204 in accordance with a third embodiment of the present invention is depicted in FIGS. 3 and 4. Interface device 204 is similar to interface device 4 in that it includes a support 224, a deformable portion 228, and an interface portion 232 that are configured in a fashion similar to those of interface device 4. It can be understood from FIGS. 3 and 4, however, that deformable portion 228 includes a plurality of deformable elements that are arranged in separate portions which are indicated at the numerals 236A, 236B, and 236C.

Support 224 includes a base 240 and further includes a pair of platforms 242A and 242B which are depicted as being oriented roughly parallel with base 240 yet being spaced therefrom. Deformable elements 236A are mutually interconnected and form a lattice structure that extends between base 240 and platform 242A, with such deformable elements 236A each having points of connection with face 240 that are spaced apart from one another and likewise having points of connection with platform 242A that are spaced apart from one another. In a similar fashion, deformable elements 246B are connected between platform 242A and platform 242B and are configured to be like deformable elements 236A. Furthermore, deformable elements 236C are similar to the deformable elements 236A and 236B, except that deformable elements 236C are connected between platform 242B and a wall 248 of interface portion 232.

It thus can be seen that deformable portion 228 includes three separately configurable deformable sub-regions that are formed by deformable elements 236A, 236B, and 236C. Depending upon the needs of the particular application, the deformable sub-regions formed by deformable elements 236A, 236B, and 236C can be of different sizes, shapes, configurations, compliances, etc., and need not be equally coextensive about the perimeter of interface device 204, depending upon the needs of the particular application.

It can further be seen from FIGS. 3 and 4 that interface portion 232 includes a barrier apparatus 256 that includes a plurality of barriers that are indicated at the numerals 260A, 260B, and 260C. Barriers 260A, 260B, and 260C are situated adjacent the pluralities of deformable elements 236A, 236B, and 236C, respectively, and are disconnected therefrom. Barrier apparatus 256 thus deforms separately from deformable portion 228 while being on the high pressure side of interface device 204, whereby barrier apparatus 256 resists the flowing of the flow of breathing gas or the exhaust thereof from patient 12 into the interstices of deformable portion 228.

It thus can be seen that interface device 204 can be configured such that its various deformable sub-regions can be separately configured with different deformation characteristics that are suited to the needs of the particular application. It is also noted that a greater or lesser number of platforms and divisions of the deformable elements of deformable portion 228 can be provided depending upon the needs of the particular application. Other variations and advantages will be apparent.

Figure 5:
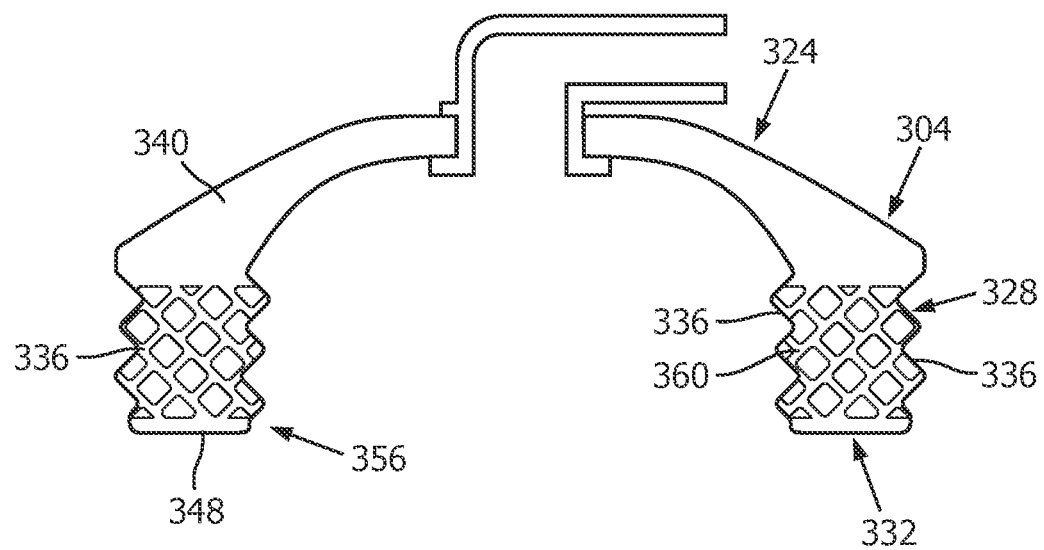
FIG. 5 is a side view, partially in section, of an interface device in accordance with a fourth embodiment of the present invention.

An interface device 304 in accordance with a fourth embodiment of the present invention is depicted generally in FIG. 5. Interface device 304 is similar to interface device 4 in that it includes a support 324, a deformable portion 328, and an interface portion 332 that are configured in a fashion similar to that of interface device 4. It is noted, however, that while deformable portion 328 includes a plurality of deformable elements 336 that are mutually interconnected and form a lattice structure that is connected between a base 340 of support 324 and a wall 348 of interface portion 332, interface portion 332 additionally includes a barrier apparatus 356 having a barrier 360 that is connected with deformable elements 336. In so doing, barrier 360 is formed by providing material within the interstices between some of the plurality of deformable element 336 in such a fashion that barrier 360 is formed at the high pressure side of deformable portion 328, which is at the inboard side of deformable portion 328. Barrier 360 thus resists the flow of breathing gas from flowing from the high pressure side of interface device 304 into the interstices between the plurality of deformable elements 336. In so doing, barrier 360 will deform together with the plurality of deformable elements 336, and thus the effect of barrier 360 on the deformation of the individual deformable elements 336 with which barrier 360 is connected, and vice-versa, must be considered in designing the overall deformation characteristics of interface device 304.

In the embodiment depicted generally in FIG. 5, barrier 360 extends along the entirety of the exterior of deformable portion 328 and thus can be said to serve as a membrane that encapsulates deformable elements 336 therein. Alternatively, and in other embodiments, barrier 360 may extend along less than the entirety of the exterior of deformable portion 328 to thereby only partially encapsulate deformable portion 328 therein. Other variations and advantages will be apparent.

Figure 6:
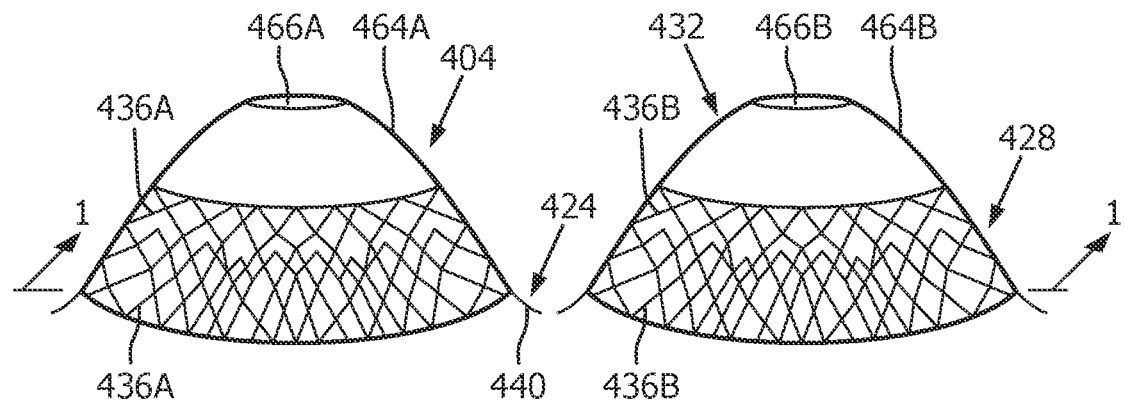
FIG. 6 is a side view of an interface device in accordance with a fifth embodiment of the present invention.
Figure 7:
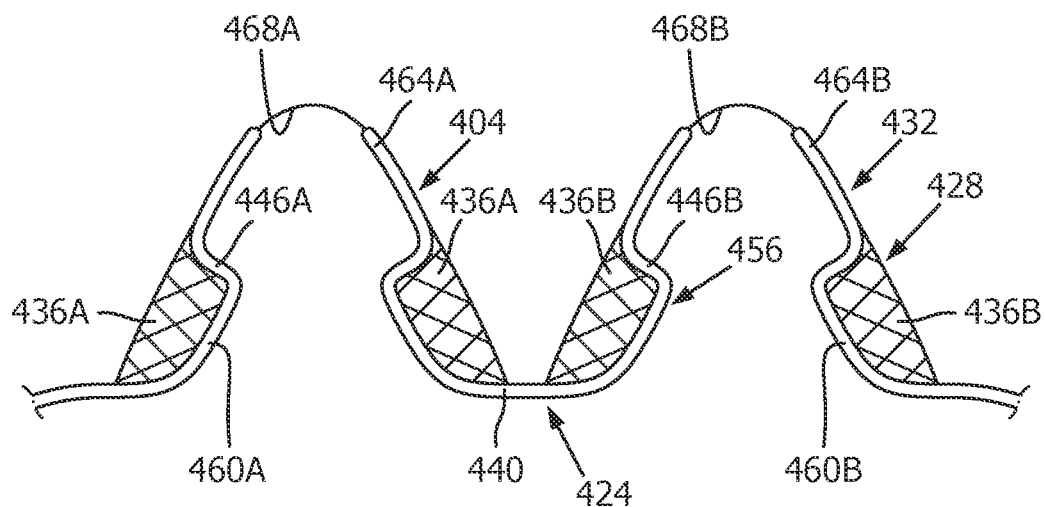
FIG. 7 is a sectional view as taken along line 7-7 of FIG. 6.

An interface device 404 in accordance with a fifth embodiment of the present invention is depicted in FIGS. 6 and 7. Interface device 404 is similar to interface device 4 in that it includes a support 424, a deformable portion 428, and an interface portion 432 that are configured in a fashion similar to that of interface device 4. It can be seen, however, that interface device 404 is a nasal pillows cushion type of device that is intended to be received in or against the nostrils of nose 20 of patient 12.

More specifically, deformable portion 428 can be said to include a plurality of deformable elements that are divided into two separate sets of deformable elements that are indicated at the numerals 436A and 436B. Deformable elements 436A are mutually interconnected and form a lattice structure, and deformable elements 436B are likewise mutually interconnected and form another lattice structure. Support 424 includes a base 440, and interface portion 432 includes a pair of walls that are indicated at the numerals 448A and 448B. interface portion 432 additionally includes a barrier apparatus 456 having a pair of barriers that are indicated at the numerals 460A and 460B.

As can be understood from FIG. 7, barriers 460A and 460B are situated on base 440, and walls 448A and 448B are situated on barriers 460A and 460B, respectively. Deformable elements 436A are connected with base 440, wall 448, and barrier 460A at a plurality of connection points that are spaced apart from one another. Likewise, deformable elements 436B are connected with base 440, wall 448B, and barrier 460B at a plurality of connection points that are spaced apart from one another.

As can further be seen in FIGS. 6 and 7, interface portion 432 further includes a pair of nozzles 464A and 464B that are situated on walls 448A and 448B, respectively, and that have a pair of openings 468A and 468B, respectively, formed therein. Nozzles 464A and 464B are of an approximately conic shape and are configured to engage the nostrils of patient 12 in nose 20. By providing deformable elements 436A and 436B connected with support 424 and interface portion 432, nozzles 464A and 464B are advantageously deformable toward and away from one another and in different directions in an advantageous fashion. Such deformation characteristics of nozzles 464A and 464B is provided by configuring deformable elements 436A and 436B to have appropriate deformation characteristics, which thereby provides enhanced fit and superior comfort when engaging the nostrils of nose 20. Other variations and advantages will be apparent.

Figure 8:
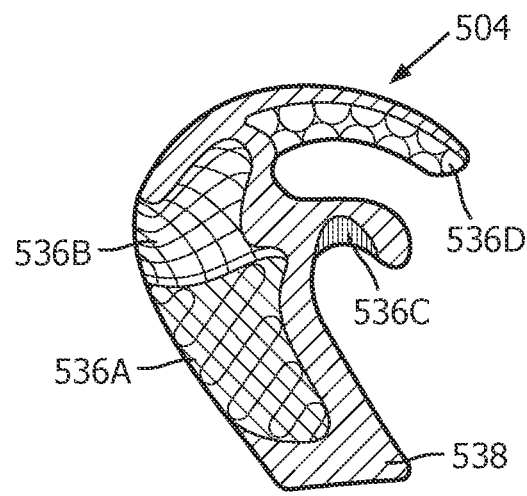
FIG. 8 is a schematic depiction of an interface device in accordance with a sixth embodiment of the present invention.

An interface device 504 in accordance with a sixth embodiment of the present invention is depicted generally in FIG. 8. Interface device 504 is similar to interface device 4 in that it includes a support, a deformable portion, and an interface portion in a fashion similar to interface device 4, and it is expressly noted that interface device 504 is intended to illustrate the further variability with which a plurality of deformable elements can be provided. Specifically, FIG. 8 depicts at least four regions of deformable elements that are indicated at the numerals 536A, 536B, 536C, and 536D, which may be collectively or individually referred to herein with the numeral 536, all of which are situated at different locations on a solid portion 538 of the support. That is, deformable elements 536A, 536B, 536C, and 536D are all formed with interstices therebetween whereas solid portion 538 generally does not have such interstices.

The deformable elements 536A are mutually interconnected and form a lattice structure that is situated adjacent a lattice structure that is formed by the mutually interconnected deformable elements 536B. Deformable elements 536C and 536D are each mutually interconnected to form a lattice structure and are each situated on other portions of solid portion 538. The variation deformation characteristics of deformable elements 536A, 536B, 536C, and 536D are selected and are customizable according to the needs of the particular application to provide enhanced comfort and fit for patient 12.

That is, and by way of example, deformable elements 536A form a first deformable portion having different compliance characteristics than a second deformable portion that is formed by deformable element 536B. Such different compliance characteristics can be achieved through the use of different materials to form the deformable elements 536A and 536B and/or by configuring the deformable elements to have different physical dimensions such as length, cross-sectional dimensions, density (i.e., spacing with respect to one another), and the like. It is expressly noted that the first deformable portion formed by deformable elements 536A and the second deformable portion formed by deformable elements 536B need not have a wall between them, and rather deformable elements 536A can be directly connected with deformable elements 536B. This can be accomplished through careful design to cause certain of deformable elements 536A to be directly connected with certain of deformable elements 536B or in other fashions. That is, the lattice structures formed by deformable elements 536A and the lattice structures formed by deformable elements 536B can be distinctly different in form and can still be situated adjacent one another without requiring an intervening wall structure to which both are connected. Rather, the lattice structures formed by deformable elements 536A and the lattice structures formed by deformable elements 536B can be directly connected together by directly connecting certain of deformable elements 536A together with certain of deformable elements 536B during the additive manufacturing formation process. As such, it can be understood that multiple different lattice structures can be directly connected together during manufacture to achieve customized physical characteristics.

Figure 9:
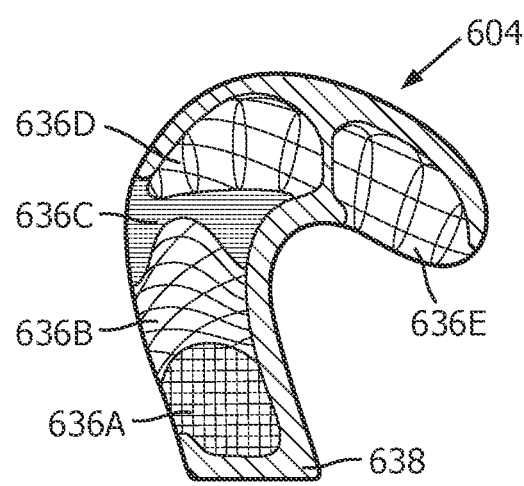
FIG. 9 is a schematic depiction of an interface device in accordance with a seventh embodiment of the present invention.
Figure 12:
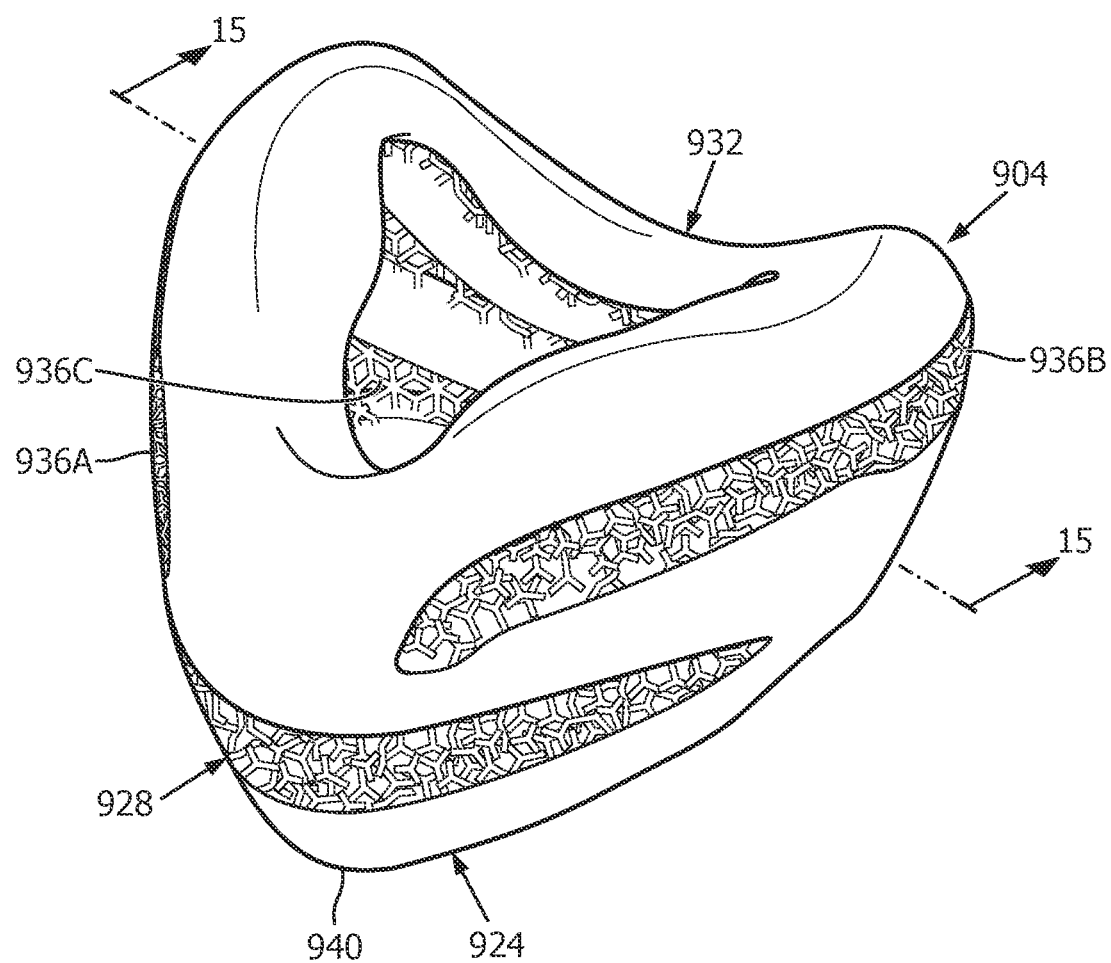
FIG. 12 is a depiction of an interface device in accordance with a tenth embodiment of the present invention.
Figure 13:
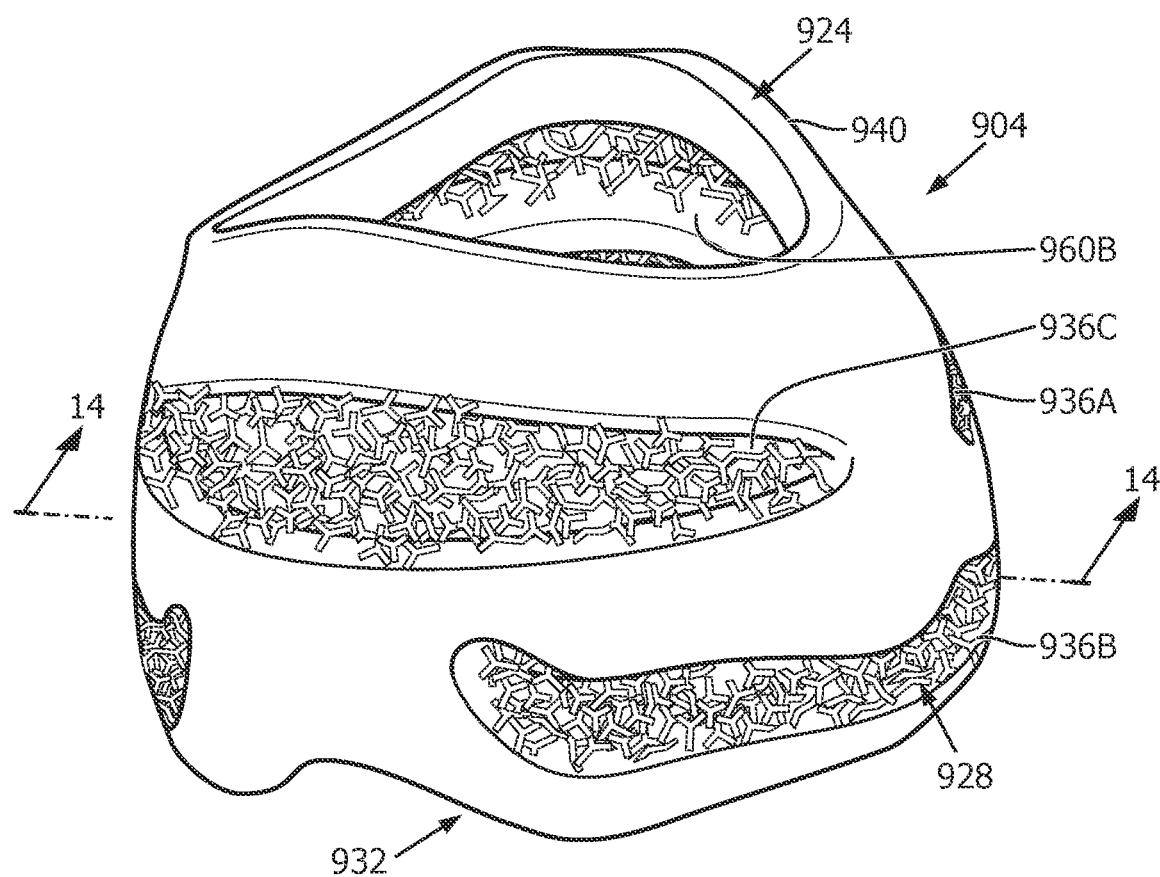
FIG. 13 is another view of the interface device of FIG. 12.
Figure 14:
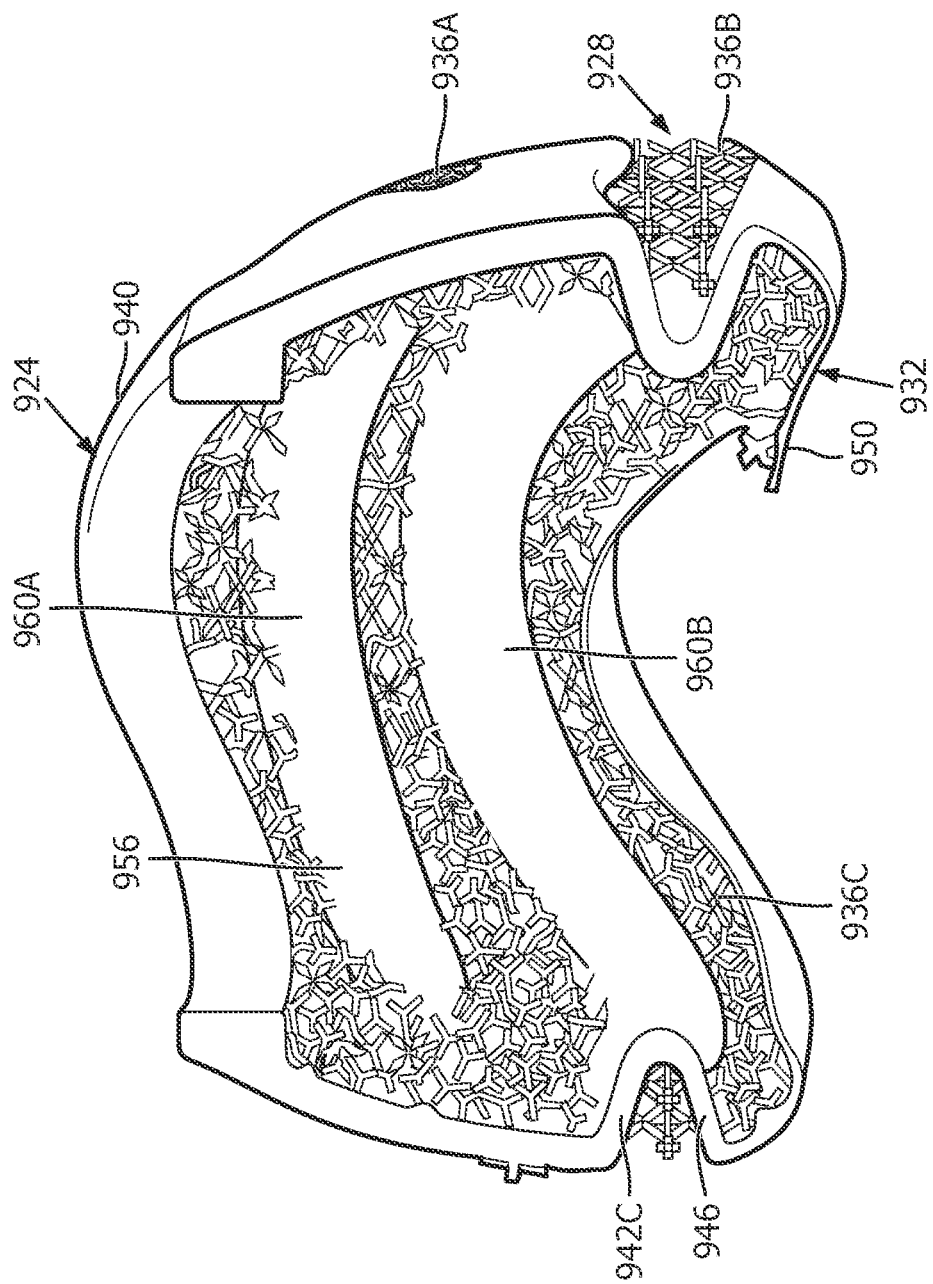
FIG. 14 is a sectional view as taken along line 14-14 of FIG. 13.
Figure 15:
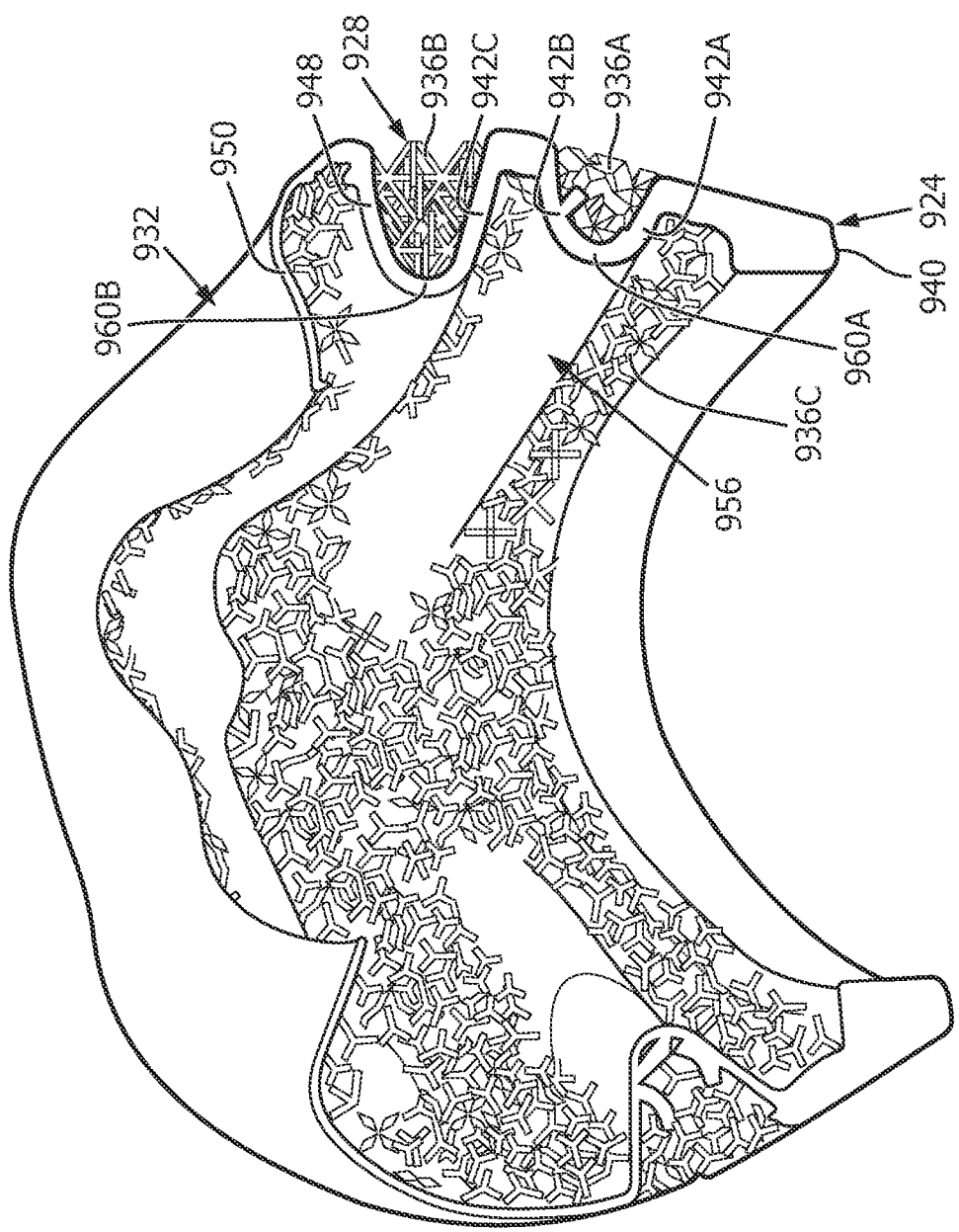
FIG. 15 is a sectional view as taken along line 15-15 of FIG. 12.

An interface device 604 in accordance with a seventh embodiment of the present invention is depicted generally in FIG. 9. Interface device 604 is similar to interface device 504 except that it includes five different sets of deformable elements 636A, 636B, 636C, 636D, and 636E, which may be collectively or individually referred to herein with the numeral 636, and all of which are situated at various locations on a solid portion 638 of the support. The arrangement of the sets of deformable elements 636 is completely different than the arrangement of the sets of deformable elements 536, and FIGS. 8 and 9 are thus intended to illustrate how the various configurations of the various deformable elements can be customized to meet the demands of any particular application with respect to desired distribution of compliance characteristics and the like in any advantageous fashion.

An interface device 704 in accordance with an eighth embodiment of the present invention is depicted generally in FIGS. 10A and 10B. More specifically, FIG. 10A depicts a solid portion 736 of a support of interface device 704, and FIG. 10B depicts four sets of deformable elements 736A, 736B, 736C, and 736D that are depicted in different arrangements on solid portion 738. Likewise, an interface device 804 in accordance with a ninth embodiment of the present invention is depicted generally in FIGS. 11A and 11B. That is, a solid portion 838 of interface device 804 is depicted in FIG. 11A, and FIG. 11B additionally depicts three sets of deformable elements 836A, 836B, and 836C situated at different locations on solid portion 838. Interface devices 704 and 804 further illustrate the variability with which the deformable portions can be configured to provide customized compliance characteristics that are suited to individual patients or to classes of patients depending upon the needs of the particular application.

By way of example, solid portions 538, 638, 738, and 838 can be formed of relatively rigid structures such as PVC and the like or can be formed of relatively compliant materials such as polymer foam or other such materials. The various deformable elements that are provided at the various locations on interface devices 504, 604, 704, and 804 can be selected to have compliance properties that are suited to the needs of individual patients or to classes of patients and that thus enable such interface devices to have improved fit and function, both of which are desirable. Other variations and advantages will be apparent.

An interface device 904 in accordance with a tenth embodiment of the present invention is depicted generally in FIGS. 12-15. Interface device 904 is similar to interface device 4 in that it includes a support 924, a deformable portion 928, and an interface portion 932 that are configured in a fashion similar to that of interface device 4.

Support 924 can be said to include a base 940, and to further include a plurality of platforms 942A, 942B, and 942C that are not necessarily oriented parallel with base 940 or with one another and rather are at various orientations with respect thereto. interface portion 932 can be said to include a wall 948, a flap 950, and a barrier apparatus 956. Barrier apparatus 956 can be said to include a pair of barriers that are indicated at the numerals 960A and 960B. Furthermore, the deformable portion 928 can be said to include a plurality of deformable elements that are, in the depicted exemplary embodiment, described herein in an exemplary fashion as being in three sets that are indicated at the numerals 936A, 936B, and 936C.

By way of example, the barrier 960A can be said to extend between and/or to include platforms 942A and 942B. In a similar fashion, barrier 960B can be said to extend between and/or to include platform 942C and wall 948. Deformable elements 936A can be said to be connected with barrier 960A and to further be connected with platforms 942A and 942B. In a similar fashion, deformable elements 936B can be said to be connected with and to extend between platform 942C, barrier 960B, and wall 948. Deformable elements 936C are elsewhere situated on interface device 4 at the high pressure side thereof.

As in all of the aforementioned embodiments, the various deformable elements 936A, 936B, and 936C are connected with the various structures of support 924 and interface portion 932 at a plurality of spaced apart connection points and are, at least in part, mutually interconnected with one another to form a lattice structure. Also, the various deformable elements 936A, 936B, and 936C of deformable portion 928 are co-formed with support 924 and interface portion 932 such that interface device 904 is integrally formed as a single piece unitary structure. The configuration of the various deformable elements of deformable portion 928 can be selected as needed to provide customized compliance characteristics that are suited to the needs of any particular application.

While barrier apparatus 956 is depicted herein as providing a barrier that resists the flow of breathing gas from flowing through the wall thereof and to the exterior of interface device 904, it is understood that in other embodiments certain portions of deformable portion 928 can be configured to permit the flow of breathing gas and/or the exhalation thereof to flow through the interstices thereof for exhaust purposes or for other purposes depending upon the needs of the particular application. Furthermore, barriers 960A and 960B and platforms 942A, 942B, and 942C may themselves be complaint deformable structures whose deformation characteristics can be custom configured to suit the particular needs presented by the shape of the face of patient 12 and/or other needs. It is also understood that the various arrangements of the aforementioned sets of deformable elements 936A, 936B, and 936C could be configured in other arrangements to provide other compliance characteristics without departing from the present concept. As with all of the aforementioned embodiments, interface device 904 can be formed using an additive manufacturing process and likely is formed out of a polymer or other appropriately deformable material as a unitary single piece structure, but other configurations are possible without departing from the spirit of the present concept.

It thus can be seen that flap 950 engages the face of patient 12 in the vicinity of mouth 16 and nose 20, and deformable elements 936C are configured to provide desirable levels of tensile and compressive compliance in order to provide an improved fit and thus improved functionality of interface device 904 with patient 12. It can further be seen that flap 950 is advantageously configured to conform to the shape of the face of patient 12 in the vicinity of the airways, and some of the deformable elements 936C extend between and are connected with wall 948 and flap 950 in a fashion to provide desirable deformation characteristics therebetween. In this regard, it can be seen that the various structures that form support 924, deformable portion 928, and interface portion 932 can have any of a variety of shapes that are suited to provide customized levels of compliance at various locations thereon in order to enhance the fit and comfort with patient 12, which provides enhanced performance. Other variations and advantages will be apparent.

Figure 16:
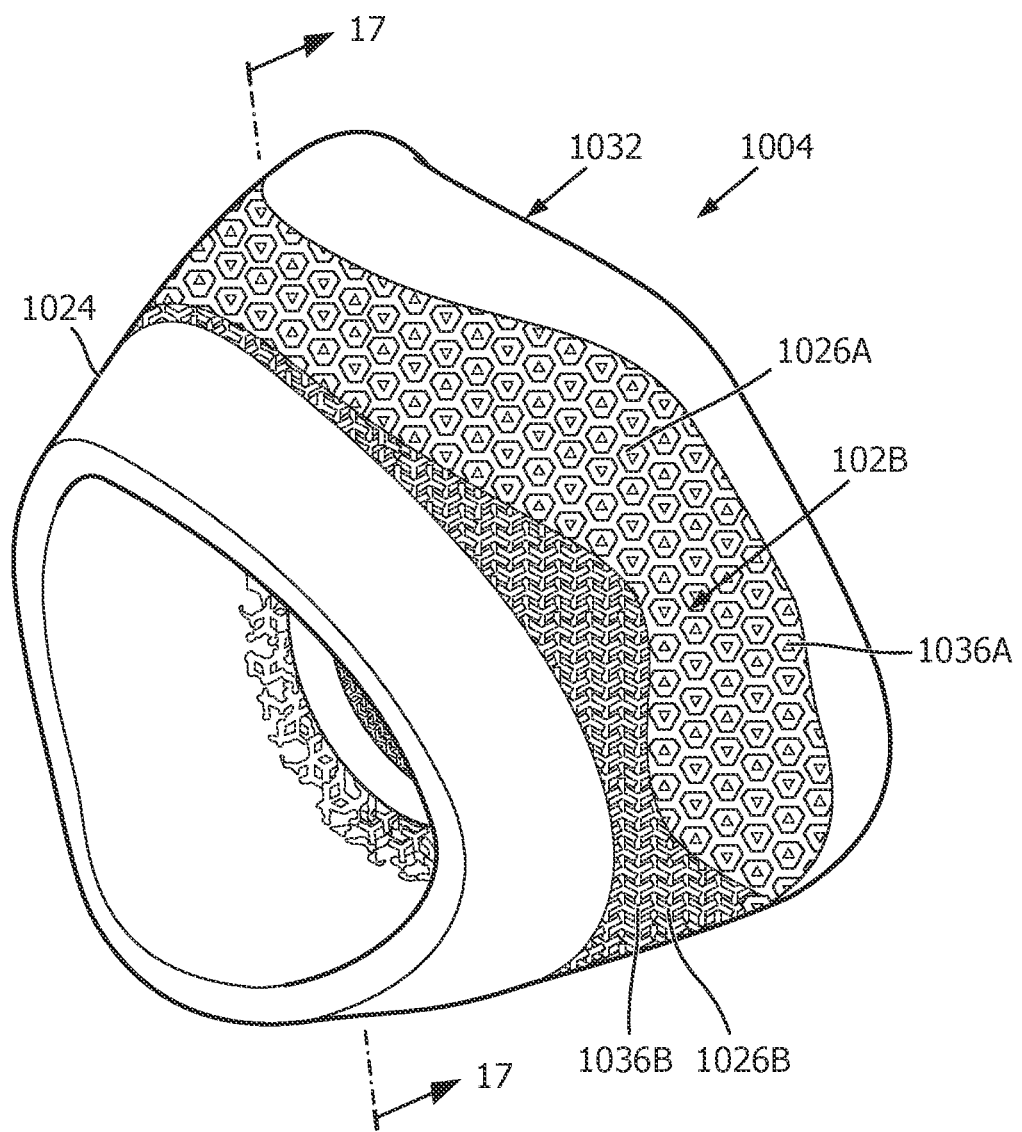
FIG. 16 is a depiction of an interface device in accordance with an eleventh embodiment of the present invention.
Figure 17:
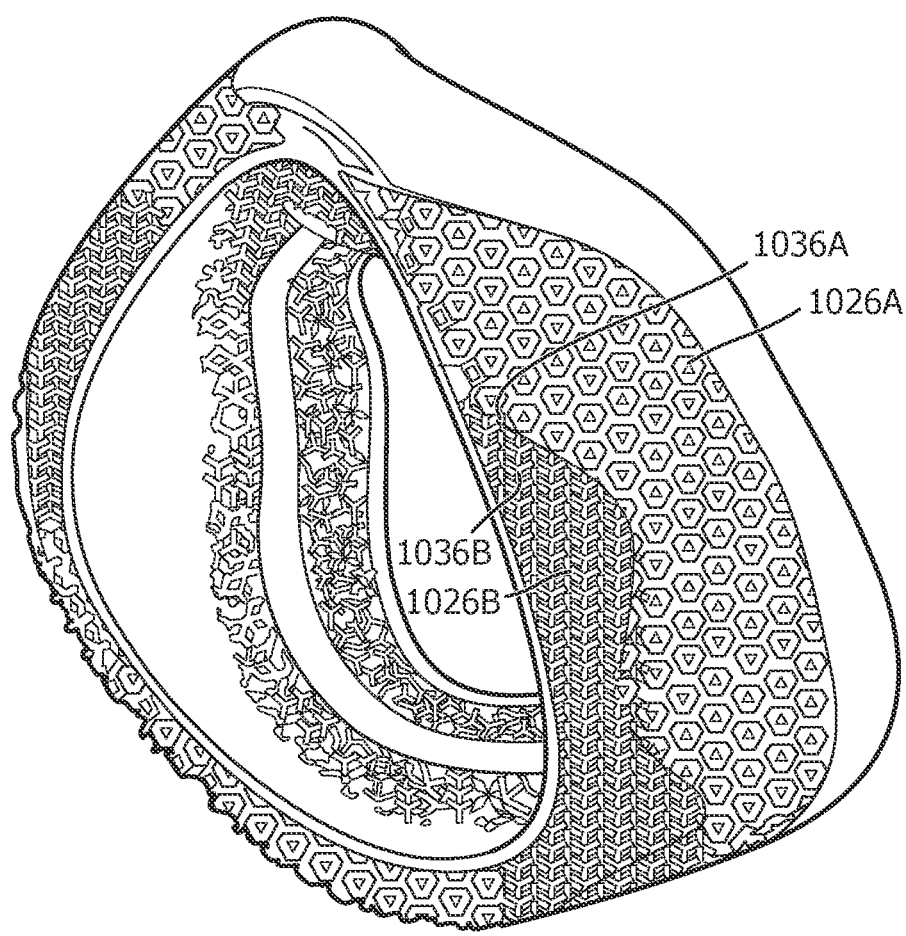
FIG. 17 is a sectional view as taken along line 17-17 of FIG. 16.

An interface device 1004 in accordance with an eleventh embodiment of the present invention is depicted generally in FIGS. 16-17. Interface device 1004 is similar to interface device 4 in that it includes a support 1024, a deformable portion 1028, and an interface portion 1032 that are configured in a fashion similar to that of interface device 4.

Deformable portion 1028 can be said to include a first deformable portion 1028A that is formed by a plurality of deformable elements 1036A and a second deformable portion 1028B that is formed by a plurality of deformable elements 1036B. The exemplary first deformable portion 1028A has different compliance properties than second deformable portion 1028B, and this is due at least in part to the fact that deformable elements 1036A are generally each of a longer length than deformable elements 1036B. Also, different materials can be employed in forming first and second deformable portions 1028A and 1028B, and/or other differences can exist therebetween. Regardless of first and second deformable portions 1028A and 1028B being distinctly different in form, certain of deformable elements 1036A are directly connected with certain of deformable elements 1036B. As such, first and second deformable portions 1028A and 1028B can be directly connected together without requiring an intervening wall or other structure to enable such connection. This is accomplished through careful design of deformable portion 1028 such that certain of deformable elements 1036A are directly connected with certain of deformable elements 1036B.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An interface device structured to be connected in fluid communication with a source of breathing gas and to provide a flow of breathing gas to the airways of a patient, the interface device comprising:
    a support;
    a deformable portion situated on the support;
    an interface portion situated on the deformable portion and being structured to be engaged with the patient at or near the airways; and
    the deformable portion comprising a plurality of deformable elements that form a lattice structure and that are connected with the support at a plurality of spaced apart points of connection on the support, the deformable portion further comprising a plurality of interstices situated between the plurality of deformable elements;
    wherein at least some of the deformable element of the plurality of deformable elements are mutually interconnected with one another;
    wherein the interface portion comprises a wall, the plurality of deformable elements being connected with the wall at a plurality of spaced apart additional points of connection on the wall;
    wherein the interface portion further comprises a barrier apparatus that includes a barrier that extends between the support and the wall and that is structured to resist the flow of breathing gas from flowing into contact with the plurality of deformable elements and that is further structured to resist the flow of breathing gas from flowing into the interstices;
    wherein the plurality of deformable elements and the plurality of interstices are encapsulated within the barrier.

2. The interface device of claim 1, wherein the wall is contoured to enable the wall to engage at least a portion of the face of the patient.

3. The interface device of claim 1, wherein the interface portion further includes a flap that protrudes from the wall and that is structured to engage the face of the patient.

4. The interface device of claim 3, wherein at least a portion of the flap is spaced from the wall to form a pocket that is structured to receive against it the flow of breathing gas as positive fluid pressure that is structured to deform the at least a portion of the flap into engagement with the face of the patient.

5. The interface device of claim 1, wherein at least some of the deformable elements of the plurality of deformable elements are connected with the barrier.

6. The interface device of claim 1, wherein the plurality of deformable elements are disconnected from the barrier.

7. The interface device of claim 1, wherein the wall of the interface portion comprises a pair of walls, the plurality of deformable elements being connected with the pair of walls at a plurality of spaced apart additional points of connection on the pair of walls, and wherein the interface portion further comprises a pair of nozzles that are situated on the pair of walls and that are structured to engage the nostrils of the patient.

8. The interface device of claim 1, wherein the support includes a base and at least a first platform, wherein a portion of the plurality of deformable elements are situated between the base and the at least first platform, and wherein another portion of the plurality of deformable elements are situated between the at least first platform and the wall.

9. The interface device of claim 1, wherein at least the deformable portion is formed via an additive manufacturing process.

10. The interface device of claim 9, wherein the deformable portion is formed from the additive manufacturing process out of a plurality of materials, at least one material of the plurality of materials having at least a first material property that is different than that of another material of the plurality of materials.

11. The interface device of claim 10, wherein the deformable portion is a matrix formed from the plurality of materials to form a composite or alloy.

* * * * *